United States Patent [19]
Tubin

[11] Patent Number: 5,390,369
[45] Date of Patent: Feb. 21, 1995

[54] MULTI-FUNCTIONAL PROTECTIVE EYEWEAR

[75] Inventor: William E. Tubin, Randolph, Mass.

[73] Assignee: Scorpion Sunglasses, Inc., Randolph, Mass.

[21] Appl. No.: 109,221

[22] Filed: Aug. 19, 1993

Related U.S. Application Data

[63] Continuation of Ser. No. 881,247, May 11, 1992, abandoned.

[51] Int. Cl.$^6$ .................................................. A61F 9/04
[52] U.S. Cl. ............................................ 2/12; 2/432; 2/446; 2/448
[58] Field of Search .................. 2/432, 446, 448, 431, 2/426, 450, 439, 12, 10, 13; 351/44, 45, 47, 158

[56] References Cited

U.S. PATENT DOCUMENTS

| | | | |
|---|---|---|---|
| 604,238 | 5/1898 | Nerney | 2/439 |
| 2,545,078 | 3/1951 | Gardner | 2/432 X |
| 3,544,204 | 12/1970 | Bienenfeld | 2/448 X |
| 4,309,775 | 1/1982 | Jory | 2/432 X |
| 4,916,754 | 4/1990 | Kang | 2/432 X |
| 4,951,316 | 8/1990 | Moody | 2/12 X |
| 5,016,292 | 5/1991 | Rademacher | 2/448 X |

*Primary Examiner*—Peter Nerbun
*Attorney, Agent, or Firm*—Morse, Altman, Dacey & Benson

[57] ABSTRACT

Protective eyewear is provided with a visor component integrally sweeping arcuately over the bridge of the nose and over both eyes between opposed extremities that are positioned rearwardly of the outer corners of both eyes, a lens component having portions sweeping arcuately across both eyes between opposed extremities that are positioned rearwardly of the outward corners of both eyes the visor component defining an arcuate groove in which the upper profile of the lens component is seated and bonded, and a pair of temple components hinged to opposite extremities of the visor component, each of the temple components including a forward part that is hinged to the visor component, and a rearward part that telescopically engages the forward part and that presents an ear engaging portion. The configuration adjustably accommodates a wide range of wearers and adaptably serves under a wide range of conditions.

10 Claims, 5 Drawing Sheets

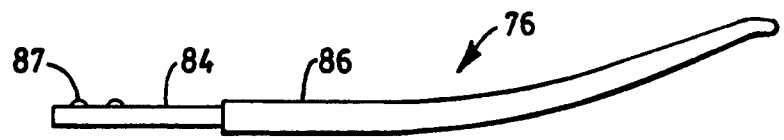
FIG. 9
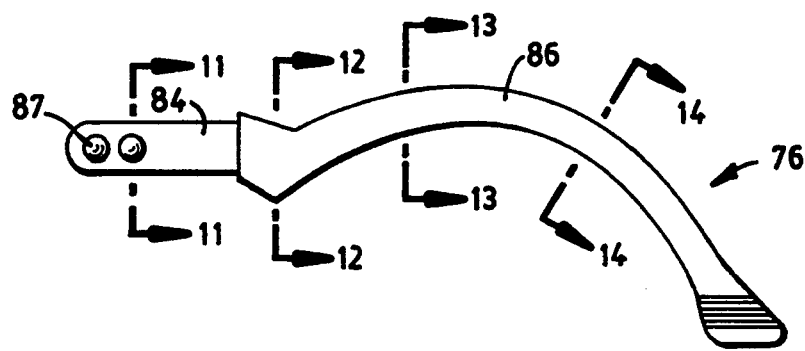
FIG. 10
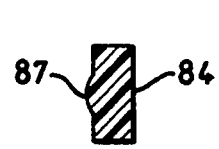 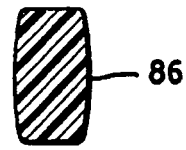
FIG. 11    FIG. 12
 
FIG. 13    FIG. 14

MULTI-FUNCTIONAL PROTECTIVE EYEWEAR

This is a continuation of application Ser. No. 07/881,247, filed on May 11, 1992, now abandoned.

1. FIELD OF THE INVENTION

The present invention relates to anti-solar and anti-glare protective eyewear and, more particularly, to multi-functional anti-solar and anti-glare protective eyewear that adjustably accommodate a wide range of wearers and that adaptably serve under a wide range of conditions.

2. BACKGROUND OF THE INVENTION

Anti-solar and anti-glare protective eyewear are often called sunglasses even though often constructed exclusively of plastic rather than glass. This eyewear is intended to offer year-round comfort and protection for the eyes against direct sunlight, direct glare, and reflected glare, and against related visible and near visible radiation including ultraviolet and near ultraviolet (blue) radiation. Typically, sunglass frames are composed of polymeric and/or metallic materials and sunglass lenses are composed of polycarbonate or glass. There have been numerous basic lens types, including constant density, photochromic, mirror, gradient and polarizing. There have been many hundreds of sunglass frame designs, some incorporating visors, that have been designed to perform specific functions which are mandated by specific light conditions and users' activities. In connection with such conditions and activities, such criteria as sunlight attenuation and impact resistance have been defined by the American Standards Institute (ANSI). The foregoing technology/industry perspective has dominated eyeglass appearance and function for many years. In the past, however, traditional eyeglass designs have continued essentially unchanged, each design being limited to particular users for particular conditions.

BRIEF SUMMARY OF THE INVENTION

The object of the present invention is to provide an eyewear design in which a particularly designed visor, a particularly designed lens, and particularly designed temple components all function interactively to provide comfort and protection for a wide range of users under a wide range of conditions. Specifically the following three features are required for performance in accordance with the present invention. The visor component integrally sweeps arcuately over the bridge of the nose and over both eyes between opposed extremities that are positioned rearwardly of the outer corners of both eyes. The lens component, in either a one-piece version for both eyes or a two-piece version for the eyes separately, sweeps arcuately across both eyes between opposed extremities that are positioned rearwardly of the outward corners of both eyes. At the rearward profile of the visor component is an arcuate groove in which the upper profile of the lens component is seated and bonded. At the center of the groove, the visor provides a pair of downwardly extending opposed tabs for reinforcement of the position of the center of the lens component in the vicinity of the bridge of the nose. At each outer extremity of the groove, the visor component provides a rearwardly extending anchor piece that carries a hinge, but tapers to an acute angle that permits free flow of air from under the visor component. Each of the temple components has forward and rearward parts. One of these parts is pivoted to this hinge. These parts telescopically mate. The rearward part snugly fits over the ear.

The design is such as to serve a variety of functions in addition to simply shielding the eyes from harmful light and glare. The visor design shields the eyes from direct exposure to the sun and permits a wearer to tilt his or her head downwardly to achieve partial or total blockage of annoying or harmful light; does not add noticeable weight or bulk; does not create imbalance; does not impede vertical field of view; ensures comfortable and secure positioning on the face while presenting an aerodynamic surface to high wind velocity and variable wind direction.

For a fuller understanding of the nature and objects of the present invention, reference is made to the following detailed specification, which is to be taken in connection with the accompanying drawings wherein:

FIG. 9 is a top plan view of one of the mating temple parts of the embodiment of FIG. 1;

FIG. 10 is a side elevation of the temple part of FIG. 9;

FIG. 11 is a cross-section, taken along the line 11—11 of FIG. 10;

FIG. 12 is a cross-section, taken along the line 12—12 of FIG. 10;

FIG. 13 is a cross-section, taken along the line 13—13 of FIG. 10;

FIG. 14 is a cross-section, taken along the line 14—14 of FIG. 10;

DETAILED DESCRIPTION OF THE PREFERRED EMBODIMENT

Figure 1:
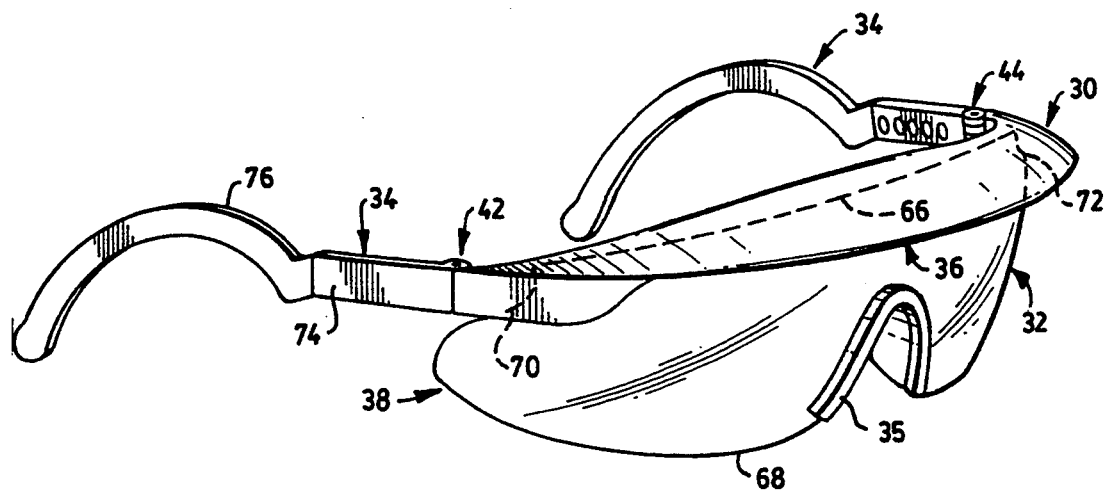
FIG. 1 is a forward perspective view of a preferred embodiment of the present invention.
Figure 2:
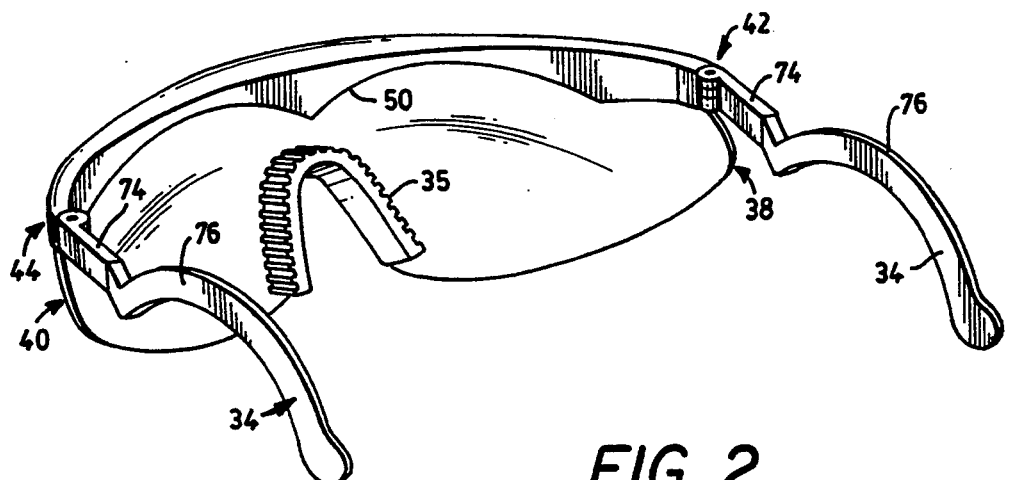
FIG. 2 is a rearward perspective view of the embodiment of FIG. 1.
Figure 3:
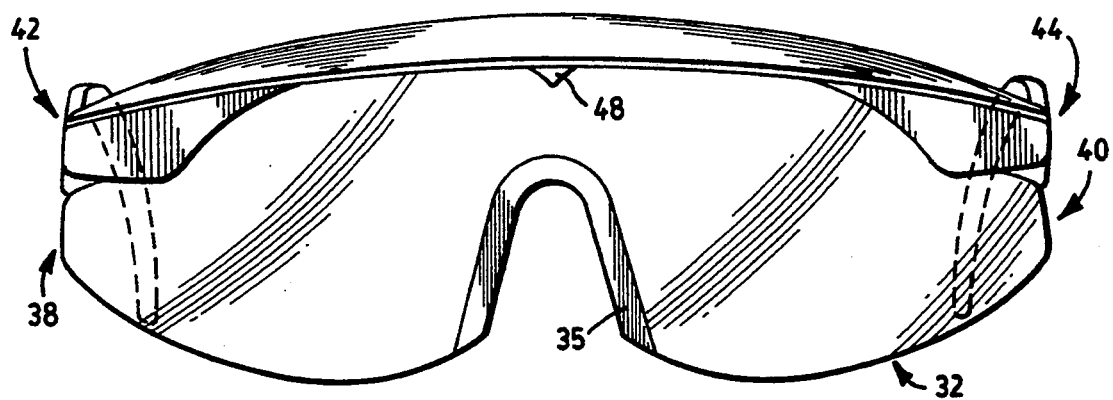
FIG. 3 is a front view of the embodiment of FIG. 1.
Figure 4:
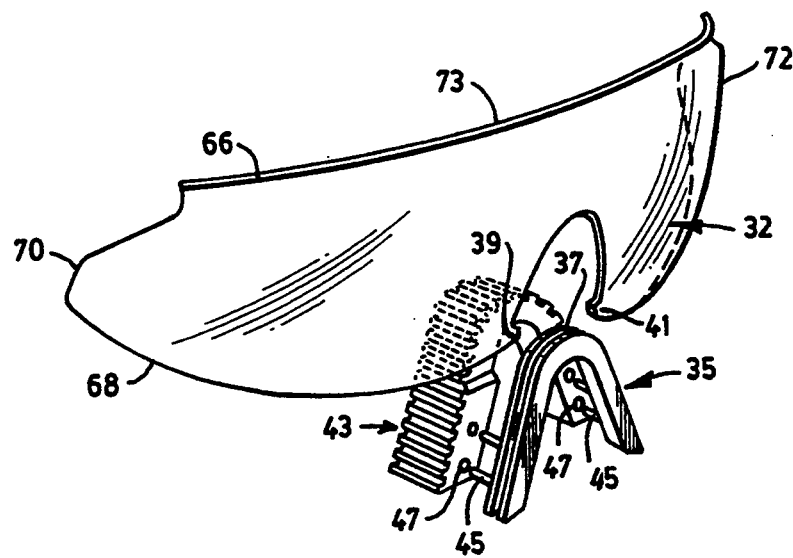
FIG. 4 is an exploded view of the lens component and nose piece component of the embodiment of FIG. 1.

As shown in FIGS. 1 and 2, the illustrated preferred embodiment comprises a fixed visor component 30, a fixed lens component 32, and a pair of adjustable temple components 34, 34. Visor component 30 integrally sweeps arcuately over the bridge of the nose as at 36 and over both eyes between opposed extremities 42, 44. Lens component 32 integrally sweeps arcuately over the bridge of the nose at 36 and across both eyes between opposed extremities 38, 40, which wrap around the head and are positioned rearwardly of the outward corners of both eyes. Opposed extremities 42, 44 of the visor component are positioned above opposed extremities 38, 40 of the lens component.

Figure 5:
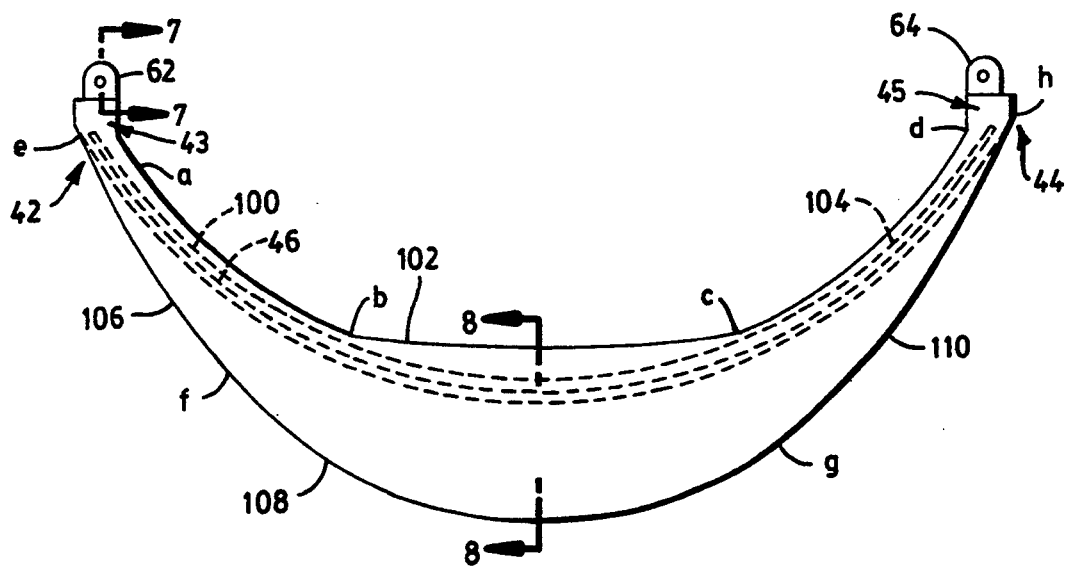
FIG. 5 is a top plan view of the visor component of the embodiment of FIG. 1.
Figure 7:
FIG. 7 is a cross-section, taken along the line 7—7 of FIG. 5.
Figure 8:
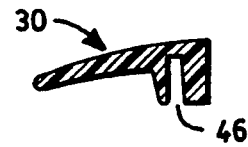
FIG. 8 is a cross-section, taken along the line 8—8 of FIG. 5.
Figure 6:
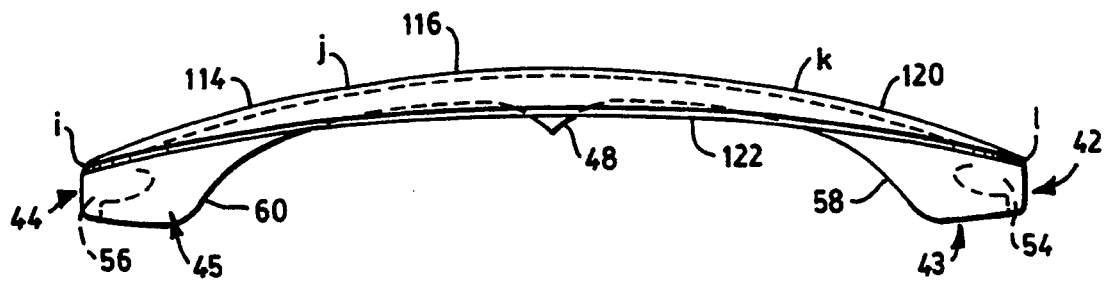
FIG. 6 is a front view of the visor component of the embodiment of FIG. 1.
Figure 15:
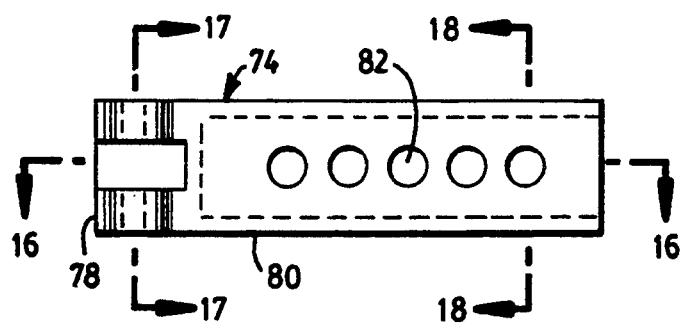
FIG. 15 is a side elevation of one of the mating temple parts of the embodiment of FIG. 1.
Figure 16:
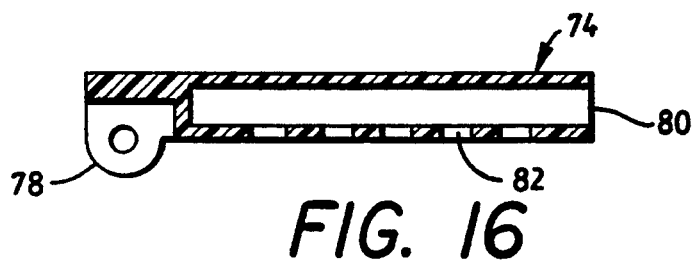
FIG. 16 is a cross-section, taken along the line 16—16 of FIG. 15.
Figure 17:
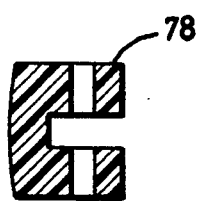
FIG. 17 is a cross-section, taken along the line 17—17 of FIG. 15.

As shown in FIG. 5, an arcuate groove 46 extends along the rearward edge of visor component 30 between extremities that are adjacent to extremities 42, 44, but that lie therebetween. In the vicinity of bridge 36, the visor includes a buttress region having a pair of downwardly depending crests 48, 50 with inner surfaces that are continuations of the inner surfaces of groove 46. In the vicinity of extremities 42, 44, the visor includes a pair of anchor regions 43, 45, which are solid at 54, 56 and bifurcated at 58, 60 to provide opposed and deepened continuations of groove 46. These anchor regions terminate before reaching a pair of rearwardly projecting journals 62, 64, which serve for pivotal attachment to the temple components in a manner to be discussed below.

Lens component 32 is an optically active curved sheet that is approximately as thick as groove 46 is wide. The upper and lower edges 66, 68 of lens component 32 converge in arcs oppositely and outwardly to vertices 70, 72. The medial portion 73 is seated in groove 46 between crests 48, 50. The outer regions in the vicinity of vertices 70, 72 are seated in bifurcated regions 58, 60 of the anchor regions and are cemented into position.

Lens component 32 is cut away at 33 to accommodate the bridge of the nose and to receive a forward nose piece 35. Nose piece 35 is reversely bent to provide a shaped surface having an outer groove 37 in which corresponding edges of lens component 32 are seated but not bonded. Forward nose piece is held in position by a pair of cusps 39, 41 in lens component 32 at the lower extremities of the opening for the nose. A rearward nose piece 43, also reversely bent, is removably attachable to forward nose piece 35 by pins 45 which can be seated in holes 47 of the rearward nose piece. The upper rim of the lens component in a horizontal plane has a lesser radius of curvature than the lower rim of lens component in a horizontal plane. In other words, the lens is configured along a conical surface of revolution about a vertical axis. Lens component 32 has an interference coating of alternate layers of different indices of refraction, which are related in thickness to the wave lengths of radiation to be attenuated and which thereby constitute a light filter.

Each of temple components 34 includes a forward part 74 and a rearward part 76. As will be described below, these parts are pivotally adjustable as a unit with respect to visor component 30 and telescopically adjustable with respect to each other.

Figure 18:
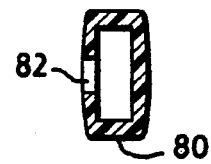
FIG. 18 is a cross-section, taken along the line 18—18 of FIG. 15.
Figure 19:
FIG. 19 is a top plan view of the forward temple part of FIG. 15.
Figure 20:
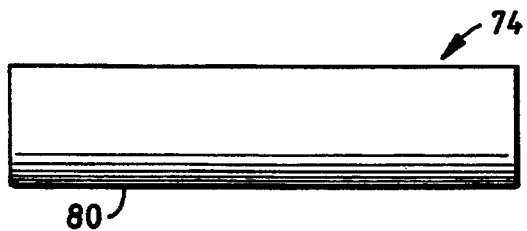
FIG. 20 is an outer side view of the forward temple part of FIG. 15.

Forward part 74, which is integral, includes a forward hinge portion 78 and a rearward receptacle portion 80. As shown in FIG. 18, the receptacle portion has a generally rectangular outer profile with upper and lower horizontal short sections and outwardly bowed vertical sections. The corresponding inner profile is truly rectangular with straight parallel upper and lower horizontal short sections, and straight vertical parallel long sections. Each forward hinge portion 78 includes a pair of ears which snugly receive one of journals 62, 64 and which include holes that register with the hole in these journals. Metal pins extend through these holes to complete the pivot. The inner section of receptacle portion 80 has a series of holes 82, five as shown in the present embodiment, for a purpose to be described below.

Rearward part 76 includes a forward elongated straight portion 84 and a rearward ear engaging curved portion 86. The forward portion, in cross section, is truly rectangular with straight horizontal upper and lower short sections, and straight vertical long side sections. The inner cross-sectional profile of receptacle portion 80 and the outer cross-sectional profile of forward elongated straight portion 84 are different only to the extent that they are enabled to reciprocate telescopically with respect to each other. The rearward portion of rearward part 76 curves inwardly and rearwardly in order to accommodate the shape of the head, and provides a hook-like configuration to accommodate the ear.

Inwardly directed from forward elongated straight portion 84 are two detent projections 86 which are characterized by the same spacing that characterizes holes 82 in receptacle portion 74. The arrangement is such that there are four secure positions at which the pair of detent projections engage a selected pair of holes, i.e. the forward pair of holes, two middle pairs of holes, and the rearward pair of holes.

EXAMPLE

The following dimensions and materials have been found to be specifically advantageous: distance between the pins at 42, 44-140 mm; maximum distance between upper and lower boundaries 66, 68 of lens component 32-47 mm; chemical composition of visor and temple components - nylon; chemical composition of nose pieces 35-Nylon, 43-polyester thermoplastic elastomer; chemical composition of lens 32-polycarbonate or glass; lens coatings, typically alternating titanium and silicon - (1) 11 strata on gray base to provide violet hue; or (2) 13 strata on brown base to produce gold hue. The radii of curvature in millimeters (mm) of various contours of the visor are as follows: radius 100 between points a and b - 80 mm; radius 102 between points b and c - 200 mm; radius 104 between points c and d - 80 mm; radius 106 between points e and f - 100 mm; radius 108 between points f and g - 60 mm; radius 110 between points g and h - 100 mm; radius 114 between points i and j - 200 mm; radius 116 between points j and k - 150 mm; radius 120 between points k and l - 200 mm; radius 122 between points i and l - 300 mm.

ALTERNATIVE EMBODIMENTS

In one alternative embodiment of the present invention, the lens is split into left and right eye parts and the nose piece is connected directly to the visor component. In another alternative embodiment, auxilliary customized lenses are bonded to the inner surfaces of the integral lens of the illustrated embodiment.

OPERATION

In operation, temple components 34 are readily adjustable to accommodate a wide range of wearers. The depth and configuration of nose piece assemblage 35, 43 cooperate with temple components 34 assist in this accommodation. The relationships among (1) radius of groove 46, which establishes the upper contour of lens 32, (2) radii 106, 110 at the forward rim of visor 30, and (3) radii 114, 120 at the upper profile of the visor, cooperate to minimize aerodynamic resistance in such a way as to maximize security of the eyewear on the face of the wearer. Specifically, the radius of curvature of the lens component is less than the radius of curvature at the outer portions of the front profile of the visor about a substantially vertical axis, and both of these radii are less than the radii of the upper and lower profiles of the visor about a substantially horizontal axis. The arrangement is such that the illustrated eyewear fits snugly and comfortably on a wide variety of wearers and maintains its position on the wearer despite a variety of ambient conditions, particularly aerodynamic conditions. The rearward part of the nose piece is adapted for ready removal from the easy forward part for cleansing and reassembly.

What is claimed is:

1. Protective eyewear comprising:
   (a) a visor component integrally sweeping arcuately over the bridge of the nose and over both eyes between opposed extremities that are positioned rearwardly of the outer corners of both eyes;
   (b) a lens component having portions sweeping arcuately across both eyes between opposed extremities that are positioned rearwardly of the outward corners of both eyes;
   (c) said visor component defining arcuate seat means in which the upper profile of said lens component is seated and bonded;
   (d) a pair of temple components hinged to opposite extremities of said visor component;
   (e) said visor component being characterized by a rearward profile and a forward profile when viewed from above its top surface, said rearward profile including opposite end portions each having a radius of curvature of approximately 80 mm and a medial portion therebetween having a radius of curvature of approximately 200 mm, said forward profile including opposite end portions each having a radius of curvature of approximately 100 mm and a medial portion therebetween having a radius of curvature of approximately 60 mm;
   (f) said front view of said visor component being characterized by an upper profile and a lower profile when viewed from adjacent its front surface, said upper profile including opposite end portions each having a radius of curvature of approximately 200 mm and a medial portion therebetween having a radius of curvature of approximately 150 mm, said low profile having a radius of curvature of approximately 300 mm.

2. Protective eyewear comprising:
   (a) a visor component integrally sweeping arcuately over the bridge of the nose and over both eyes between opposed extremities that are positioned rearwardly of the outer corners of both eyes;
   (b) a lens component having portions sweeping arcuately across both eyes between opposed extremities that are positioned rearwardly of the outward corners of both eyes;
   (c) said visor component defining an arcuate groove in which the upper profile of said lens component is seated and bonded; and
   (d) a pair of temple components hinged to opposite extremities of said visor component;
   (e) each of said temple components including a forward part that is hinged to said visor component, and a rearward part that telescopically engages said forward part and that presents an ear engaging portion;
   (f) said visor component being characterized by a rearward profile and a forward profile when viewed from above its top surface, said rearward profile including opposite end portions each having a radius of curvature of approximately 80 mm and a medial portion therebetween having a radius of curvature of approximately 200 mm, said forward profile including opposite end portions each having a radius of curvature of approximately 100 mm and a medial portion therebetween having a radius of curvature of approximately 60 mm;
   (g) said visor component being characterized by an upper profile and a lower profile when viewed from adjacent its front surface, said upper profile including opposite end portions each having a radius of curvature of approximately 200 mm and a medial portion therebetween having a radius of curvature of approximately 150 mm, said lower profile having a radius of curvature of approximately 300 mm.

3. The protective eyewear of claim 2 wherein said visor component includes at its opposite extremities a pair of anchor components having solid portions that present journals, and bifurcated portions that constitute continuations of said arcuate groove.

4. The protective eyewear of claim 2 wherein said forward part of each of said temple components provides a series of holes of predetermined spacing.

5. The protective eyewear of claim 4 wherein said rearward part of each of said temple components provides a pair of inwardly directed projections of predetermined spacing for engagement with said holes.

6. The protective eyewear of claim 4 wherein (1) said lens is characterized by a first radius of curvature, (2) the front profile of said visor is characterized by a second radius of curvature, and (3) the upper and lower profiles of said visor component are characterized by third and fourth radii of curvature, said first radius of curvature and said second radius of curvature being less than each of said third radius of curvature and said fourth radius of curvature.

7. Protective eyewear comprising:
   (a) a visor component integrally sweeping arcuately over the bridge of the nose and over both eyes between opposed extremities that are positioned rearwardly of the outer corners of both eyes;
   (b) a lens component integrally sweeping arcuately over the bridge of the nose and across both eyes between opposed extremities that are positioned rearwardly of the outward corners of both eyes;
   (c) said visor component defining an arcuate groove in which the upper profile of said lens component is seated and bonded; and
   (d) a pair of temple components hinged to opposite extremities of said visor component;
   (e) each of said temple components including a forward part that is hinged to said visor component, and a rearward part that telescopically engages said forward part and that presents an ear engaging portion;
   (f) said visor component including at its opposite extremities a pair of anchor components having solid portions that present journals, and bifurcated portions that constitute continuations of said arcuate groove;
   (g) said forward part of each of said temple components having a series of holes of predetermined spacing;
   (h) said rearward part of each of said temple components providing a pair of inwardly directed projections of predetermined spacing for engagement with said holes.
(i) (1) said lens being characterized by a first radius of curvature, (2) the front profile of said visor being characterized by a second radius of curvature, and (3) the upper and lower profiles of said visor component being characterized by third and fourth radii of curvature, said first radius of curvature and said second radius of curvature being less than each of said third radius of curvature and said fourth radius of curvature;
(j) said visor being characterized by a rearward profile and a forward profile when viewed from above its top surface, said rearward profile including opposite end portions each having a radius of curvature of approximately 80 mm and a medial portion therebetween having a radius of curvature of approximately 200 mm, said forward profile including opposite end portions each having a radius of curvature of approximately 100 mm and a medial portion therebetween having a radius of curvature of approximately 60 mm;
(k) said visor being characterized by an upper profile and a lower profile when viewed from adjacent its front surface, said upper profile including opposite end portions each having a radius of curvature of approximately 200 mm and a medial portion therebetween having a radius of curvature of approximately 150 mm, said low profile having a radius of curvature of approximately 300 mm.

8. The protective eyewear of claim 7 wherein said lens component is coated with a series of optical interference strata.

9. The protective eyewear of claim 8 wherein said series of optical interference layer includes titanium strata and germanium strata.

10. Protective eyewear comprising:
(a) a fixed visor component;
(b) a fixed lens component; and
(c) a pair of adjustable temple components;
(d) said lens component integrally sweeping arcuately over the bridge of the nose and across both eyes between first opposed extremities which wrap around the head and are positioned rearwardly of the outward corners of both eyes;
(e) said visor component integrally sweeping arcuately over the bridge of the nose and over both eyes between second opposed extremities which are positioned above said first opposed extremities;
(f) an arcuate groove extending along the rearward edge of said visor component between said second extremities; and
(g) in the vicinity of said bridge, said visor component including a buttress region having a pair of downwardly depending crests with inner surfaces that are continuations of the inner surfaces of said groove;
(h) in the vicinity of said second opposed extremities, said visor component including a pair of anchor regions which are solid at their outer limits and which are bifurcated inwardly thereof to provide opposed and broadened continuations of said groove;
(i) said anchor regions including a pair of rearwardly projecting journals;
(j) said lens component being an optically active curved sheet that is approximately as thick as said groove is wide;
(k) the upper and lower edges of said lens component converging to oppositely and outwardly directed vertices;
(l) the medial portion of said lens component being seated in said groove between said crests;
(m) said vertices being seated in said bifurcated regions;
(n) said lens component being cut away to accommodate the bridge of the nose;
(o) a nose piece that is reversely bent to provide a shaped inner surface to contact the nose and a grooved outer surface seat in which edges of said lens component are seated;
(p) said lens component having an interference coating of alternate layers having different indices of refraction, which are related in thickness to the wave lengths of radiation to be attenuated and which thereby constitute a light filter;
(q) each of said temple components including a forward part and a rearward part;
(r) said parts being pivotally adjustable as a unit with respect to said visor component and telescopically adjustable with respect to each other;
(s) said forward part including a forward hinge portion and a rearward receptacle portion;
(t) each forward hinge portion including a pair of ears which snugly receive said journal and which include holes that register with a hole in said journal;
(u) pins extending through said holes to constitute a pivot;
(v) the inner section of said receptacle portion having a series of holes;
(w) said rearward part including a forward elongated straight portion and a rearward ear engaging curved portion;
(x) the inner cross-sectional profile of said receptacle portion and the outer cross-sectional profile of said forward portion of said rearward part being different only to the extent that they are enabled to reciprocate telescopically with respect to each other;
(y) the rearward portion of said rearward part curving inwardly and rearwardly in order to accommodate the shape of the head and providing a hook-like configuration to accommodate the ear;
(z) a pair of detent projections inwardly directed from said forward portion of said rearward part;
(aa) said detent projections being characterized by the same spacing that characterizes said holes in said receptacle portion, whereby there are a plurality of secure positions at which said pair of detent projections engage a selected pair of said holes in said receptacle portion;
(ab) said visor being characterized by a rearward profile and a forward profile, said rearward profile including opposite end portions each having a radius of curvature of approximately 80 mm, and a medial portion therebetween having a radius of curvature of approximately 200 mm, said forward profile including opposite end portions each having a radius of curvature of approximately 100 mm and a medial portion therebetween having a radius of curvature of approximately 60 mm;
(ac) said visor being characterized by an upper profile and a lower profile when viewed from adjacent its front surface, said upper profile including opposite end portions each having a radius of curvature of approximately 200 mm and a medial portion therebetween having a radius of curvature of approximately 150 mm, said lower profile having a radius of curvature of approximately 300 mm.

* * * * *